(12) United States Patent
Swanson

(10) Patent No.: US 8,585,624 B2
(45) Date of Patent: Nov. 19, 2013

(54) DYNAMIC STABILIZING KNEE SUPPORT SYSTEM

(75) Inventor: Robert Scott Swanson, Winona Lake, IN (US)

(73) Assignee: S/S Dynamics, LLC, Winona Lake, IN (US)

( * ) Notice: Subject to any disclaimer, the term of this patent is extended or adjusted under 35 U.S.C. 154(b) by 323 days.

(21) Appl. No.: 13/027,550

(22) Filed: Feb. 15, 2011

(65) Prior Publication Data

US 2011/0201983 A1    Aug. 18, 2011

Related U.S. Application Data

(60) Provisional application No. 61/338,237, filed on Feb. 16, 2010.

(51) Int. Cl.
*A61F 5/00*    (2006.01)

(52) U.S. Cl.
USPC .......................................................... 602/16

(58) Field of Classification Search
USPC ....................... 602/26, 23, 16, 5, 1
See application file for complete search history.

(56) References Cited

U.S. PATENT DOCUMENTS

| | | | |
|---|---|---|---|
| 1,587,508 A | 6/1926 | Coats | |
| 3,046,981 A | 7/1962 | Biggs, Jr. et al. | |
| 3,945,046 A | 3/1976 | Stromgren | |
| 4,240,414 A | 12/1980 | Theisler | |
| 4,489,718 A | 12/1984 | Martin | |
| 4,991,571 A | 2/1991 | Kausek | |
| 5,512,039 A | 4/1996 | White | |
| 5,741,220 A * | 4/1998 | Brink | 602/14 |
| 5,857,989 A | 1/1999 | Smith, III | |
| RE37,297 E | 7/2001 | Smith, III | |
| 6,436,066 B1 * | 8/2002 | Lockhart | 602/26 |
| 6,610,023 B2 | 8/2003 | Steponovich | |
| 7,198,610 B2 | 4/2007 | Ingimundarson et al. | |
| 7,473,236 B1 * | 1/2009 | Mathewson | 602/62 |
| 7,597,675 B2 | 10/2009 | Ingimundarson et al. | |
| 7,905,851 B1 * | 3/2011 | Bledsoe | 602/26 |
| 8,328,746 B2 * | 12/2012 | Ingimundarson et al. | 602/26 |
| 2002/0010410 A1 | 1/2002 | Steponovich | |
| 2008/0287849 A1 | 11/2008 | Zukowski | |
| 2009/0099562 A1 | 4/2009 | Ingimudarson et al. | |

FOREIGN PATENT DOCUMENTS

WO    WO 94/00082    1/1994

OTHER PUBLICATIONS

DonJoy; OA Assist Knee Osteoarthritis Brace; 2009; 2 pages.
Tagg Industries; IsoDyn Aligning System; 1995; 4 pages.

* cited by examiner

*Primary Examiner* — Patricia Bianco
*Assistant Examiner* — Tarla Patel
(74) *Attorney, Agent, or Firm* — Barnes & Thornburg LLP

(57) ABSTRACT

A knee brace assembly with a proximal compression system adapted to be secured to the thigh and a distal compression system adapted to be secured to the calf. The brace includes lateral and distal hinge assemblies connecting the proximal compression system and the distal compression system to permit rotational movement of the proximal compression system with respect to the distal compression system. At least one inelastic strap extends around the proximal compression system and the distal compression system. The strap is leveraged to tighten the proximal compression system and the distal compression system to compress soft tissue in the thigh and calf when the leg is extended, but to release the proximal compression system and the distal compression system when the leg is in flexion.

21 Claims, 15 Drawing Sheets

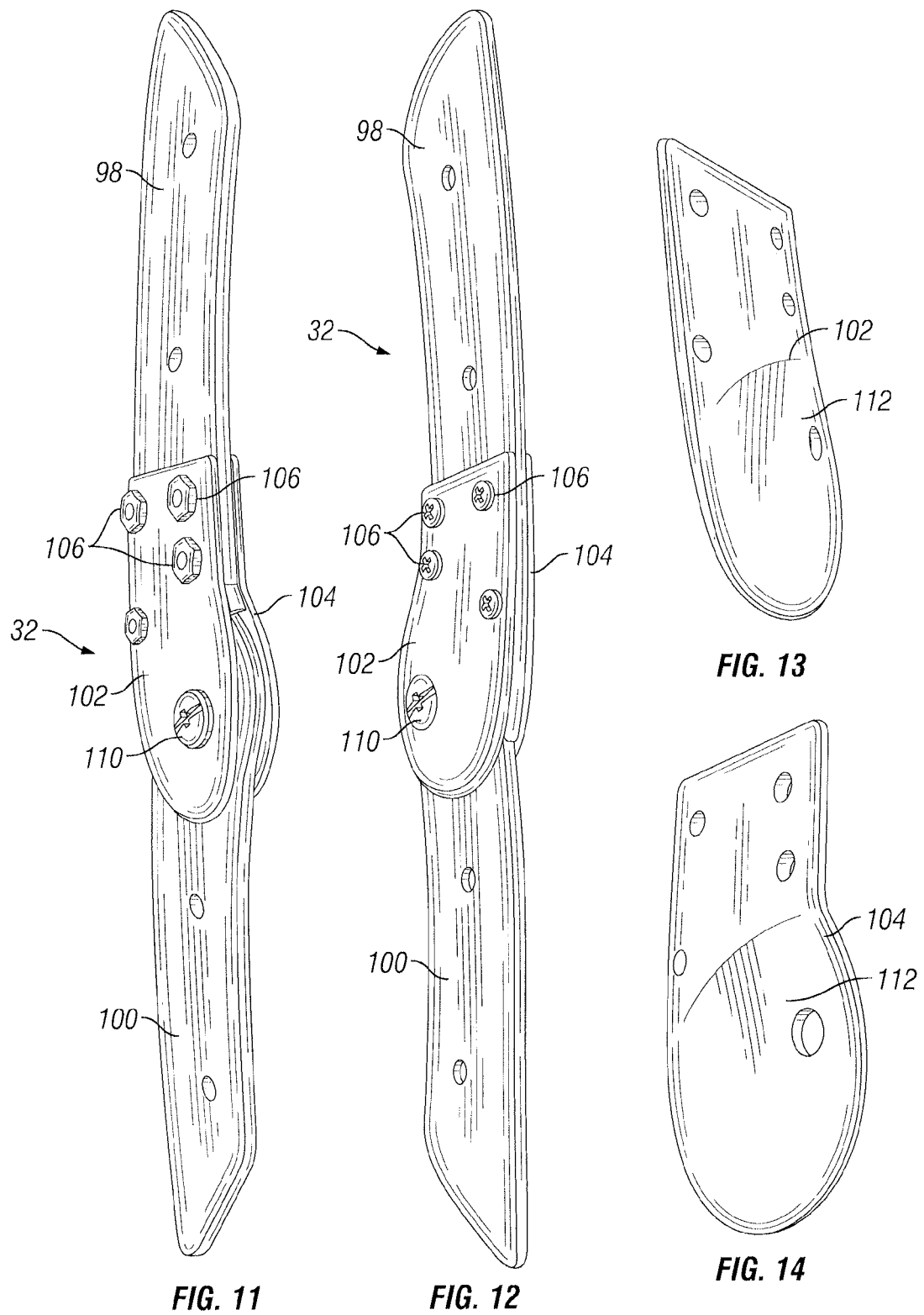

DYNAMIC STABILIZING KNEE SUPPORT SYSTEM

RELATED APPLICATION

This application claims the benefit of U.S. Provisional Application No. 61/338,237 filed Feb. 16, 2010 for a "Dynamic Stabilizing Knee Support System," the entire disclosure of which is hereby incorporated by reference.

TECHNICAL FIELD

This invention relates generally to knee braces and more particularly to a knee brace that may be customized to meet different levels of stability needs.

BACKGROUND

Knee braces are often used for people who have had soft tissue tearing and subsequent soft tissue reconstruction surgery to repair the ligament and rebalance the joint back to close to normal stability. This often leaves the user in a position to require a brace when playing sports to protect from further injury. Existing reconstruction techniques have been successful in restoring stability; however, due to anatomy and physiological differences of different users, the need for a brace is still real.

One of the problems with existing rigid braces is that this is often more bracing than what is really needed for people who have had soft tissue reconstruction. Generally upper level brace designs use some form of a rigid frame, cuffs, metal mechanically tracking hinges and a variety of strapping placed around the frame to restrict or limit movement of the proximal tibia during play to protect against subsequent injury. Additionally, existing designs do not have adjustable stability levels. Instead, the braces come in a "one level fits all needs" and the many people do not need this level of bracing.

Rigid bracing problems occur because the frame and hinge do not use anatomic methods for stability and restrict naturally kinematic movements. The leg and knee are a dynamic functioning system; attaching a rigid frame does not allow natural independent movement of the thigh and calf and the hinge does not allow natural rotation of the tibia on the femur during flexion. This creates a constrained joint and restricts the natural kinematic movement. This constraint creates problems during activity by restricting mobility/agility causing the inability to pivot turn—because the frame will not flex and let it occur. Additionally, the leg fights the brace for freedom of movement causing the brace to move around on the user's leg. This creates an unnatural binding feeling that causes the brace to migrate around, which results in the user constantly fidgeting with the brace.

After using the brace, the user becomes disenchanted with it—quits using the brace and either quits their desired level of play or tries a soft support that cannot provide enough protection to prevent further injury. This leaves the user without an available support to fit their specific needs. This identifies another problem. Existing choices of braces are either too much bracing—"over kill" or soft neoprene type products or, "not allow enough stabilizing support." This leaves a problem for people and identifies major market needs.

SUMMARY

According to one aspect, the present invention relates to a knee brace assembly that provides a user's leg with superior mobility to perform without restrictions of existing braces, which permits the user to enjoy pre-injury applications. In one embodiment, the knee brace assembly includes a proximal compression system adapted to be secured to the thigh and a distal compression system adapted to be secured to the calf. The brace includes lateral and distal hinge assemblies connecting the proximal compression system and the distal compression system to permit rotational movement of the proximal compression system with respect to the distal compression system so the thigh and calf may move independently. At least one inelastic strap extends around the proximal compression system and the distal compression system. The strap is leveraged to tighten the proximal compression system and the distal compression system to compress soft tissue in the thigh and calf when the leg is extended, but to release the proximal compression system and the distal compression system when the leg is in flexion. This provides anatomic stability and movement to provide upper levels of stability.

In one embodiment, the hinge assembly provides a natural movement that allows the thigh and calf to move independently to allow the tibia to rotate on the femur when the leg is in flexion, but stabilizes in extension. This removes the binding sensation to provide a greater sense of stability for the user along with reducing possible migration of the brace along the user's leg. For example, the hinge assemblies may include a cam surface that restricts movement to a single axis when the leg is extended, but allows movement in more than one axis when the leg is in flexion.

Embodiments are contemplated in which the brace may be customized to meet different levels of stability needs. For example, the compression systems may include compression plates that can be used to set the stability of the brace. There could be a plurality of compression plates, for example, that have various levels of stiffness and density. Although the compression plates are typically made of plastic, in one embodiment, a metal add-on connector may be provided to increase stability. This allows the system to change stability levels to different levels of sport demand, which is a feature currently missing from existing knee braces. Additionally, a physician could change levels of stability during the rehab process and provide a recommended configuration for long term use. Moreover, embodiments are contemplated in which the size of the compression systems could be adjusted to allow for various sizes of thighs and calves of users. This type of sizing changeability allows the design to be "off the shelve" without custom fitting.

Additional features and advantages of the invention will become apparent to those skilled in the art upon consideration of the following detailed description of the illustrated embodiment exemplifying the best mode of carrying out the invention as presently perceived. It is intended that all such additional features and advantages be included within this description and be within the scope of the invention.

BRIEF DESCRIPTION OF THE DRAWINGS

The present disclosure will be described hereafter with reference to the attached drawings which are given as non-limiting examples only, in which:

FIGS. 11 and 12 are perspective views of the example hinge assembly shown in FIG. 8;

FIGS. 13 and 14 are examples of inside and outside hinge plates with cam surfaces according to an embodiment of the invention;

Figure 1:
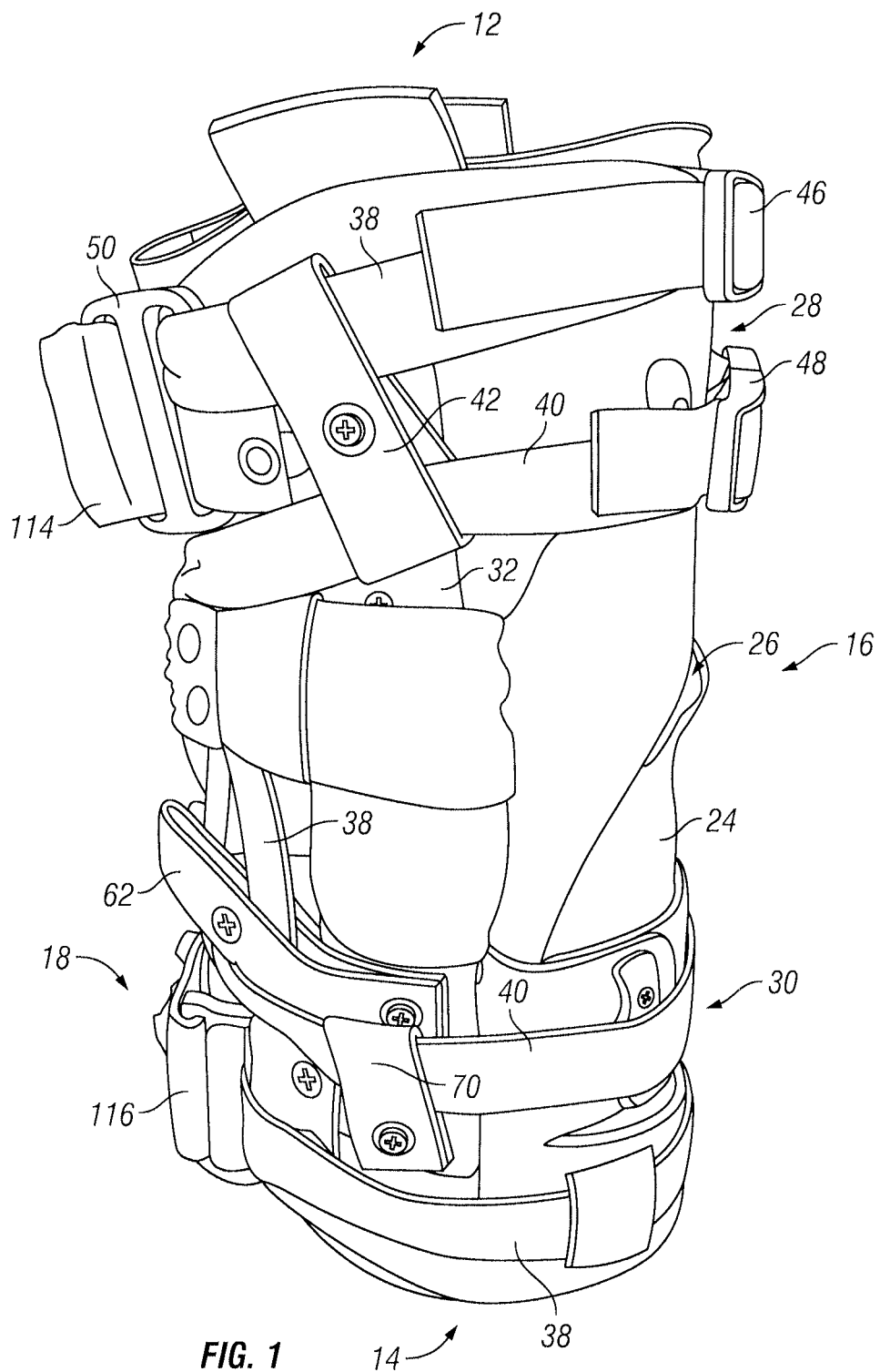
FIG. 1 is a perspective view of a knee brace assembly according to an embodiment of the present invention.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

The present invention concerns an improved knee brace. Accordingly, FIG. 1 depicts an embodiment of the knee brace assembly, shown generally at 10. For purposes of orientation, general anatomic terms will be used herein to describe the knee brace assembly 10. Thus, the knee brace assembly 10 will be described with respect to a proximal end 12, distal end 14, a medial side 16, a lateral side 18, an anterior side 20, and a posterior side 22.

In the example knee brace assembly 10 shown in FIG. 1, a flexible sleeve 24, such as a neoprene sleeve, is provided to be wore by the user; as shown, the sleeve 24 includes an optional opening 26 configured to approximately align with the user's knee cap. The sleeve 24 is removable from the knee brace assembly 10 and may be replaced.

A proximal compression system 28 is pivotally connected with a distal compression system 30 via a hinge assembly 32. The proximal compression system 28 is intended to be secured to the user's thigh (See FIGS. 14-19). The distal compression system is intended to be secured to the user's calf (See FIGS. 14-19).

In the configuration shown in FIG. 1, a first inelastic strap 38 and a second inelastic strap 40 extend around the proximal compression system 28 through a proximal lateral strap capture 42 and proximal medial strap capture 44 (FIG. 2) to the posterior side of the knee brace assembly 10. In one embodiment, the straps 38, 40 may be made of nylon. As shown, a first strap buckle 46 and a second strap buckle 48 attach the straps 38, 40. In this example, the buckles 46, 48 allow adjustability to the length of the straps 38, 40 so that compression can be adjusted as desired. As shown, the first strap 38 extends from the proximal lateral strap capture 42 through a lateral attachment anchor 50 to the posterior of the knee brace assembly 10. In the example shown, FIG. 1 also shows the first strap 38 and the second strap 40 extending back from the posterior side 22 of the knee brace assembly 10 to the anterior side 20 around the distal compression system 30. As discussed below, the configuration of the first strap and the second strap may be adjusted depending on the user's needs. For example, in the strap configuration shown in FIGS. 14-19 only the second strap 40 extends around the distal compression system 30.

Figure 2:
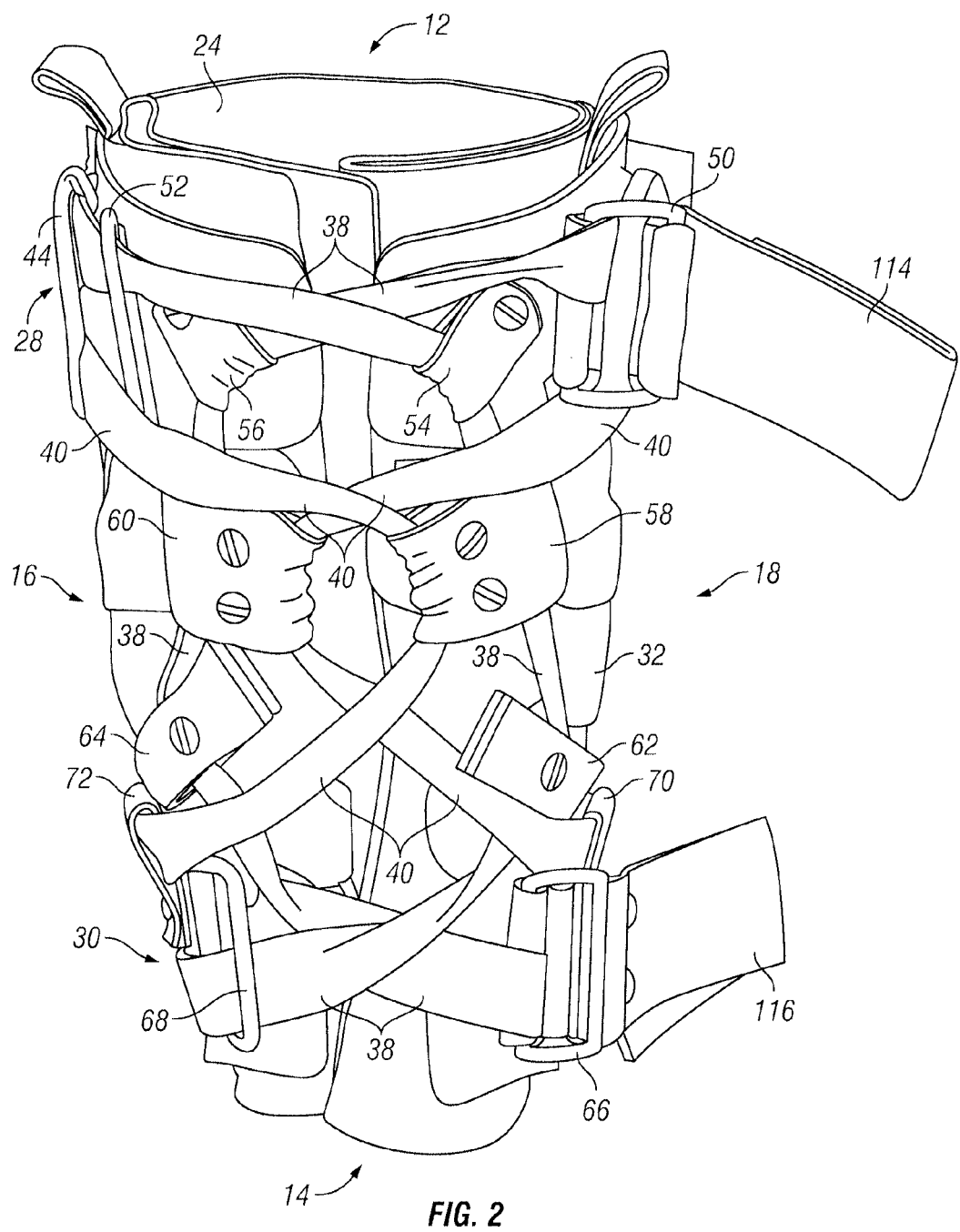
FIG. 2 is a posterior view of the example knee brace assembly shown in FIG. 1.

FIG. 2 shows an example route of the first strap 38 and the second strap 40 on the posterior side 22 of the knee brace assembly 10. In this example, the first strap 38 wraps around the proximal compression system 28 and routes through the lateral attachment anchor 50 and medial closure loop 52 so that the lateral and medial sides of the first strap 38 cross over and extend through the proximal lateral strap capture 54 and proximal medial strap capture 56, respectively. The first strap 38 passes through the lateral leverage strut anchor 58 and medial leverage strut anchor 60. As shown, the first strap 38 then passes through the distal lateral strap strut anchor 62 and the distal medial strap strut anchor 64. The first strap 38 then crosses and passes through a distal lateral attachment anchor 66 and a distal medial closure loop 68 around to the anterior side of the distal compression system 30.

In the example shown in FIG. 2, the second strap 40 crosses around the posterior of the brace assembly 10 and passes through the lateral leverage strut anchor 58 and the medial leverage strut anchor 60. The second strap 40, in this example configuration, extends around the anterior side of the distal compression system 30 through a distal lateral strap capture 70 and a distal medial strap capture 72.

Figure 3:
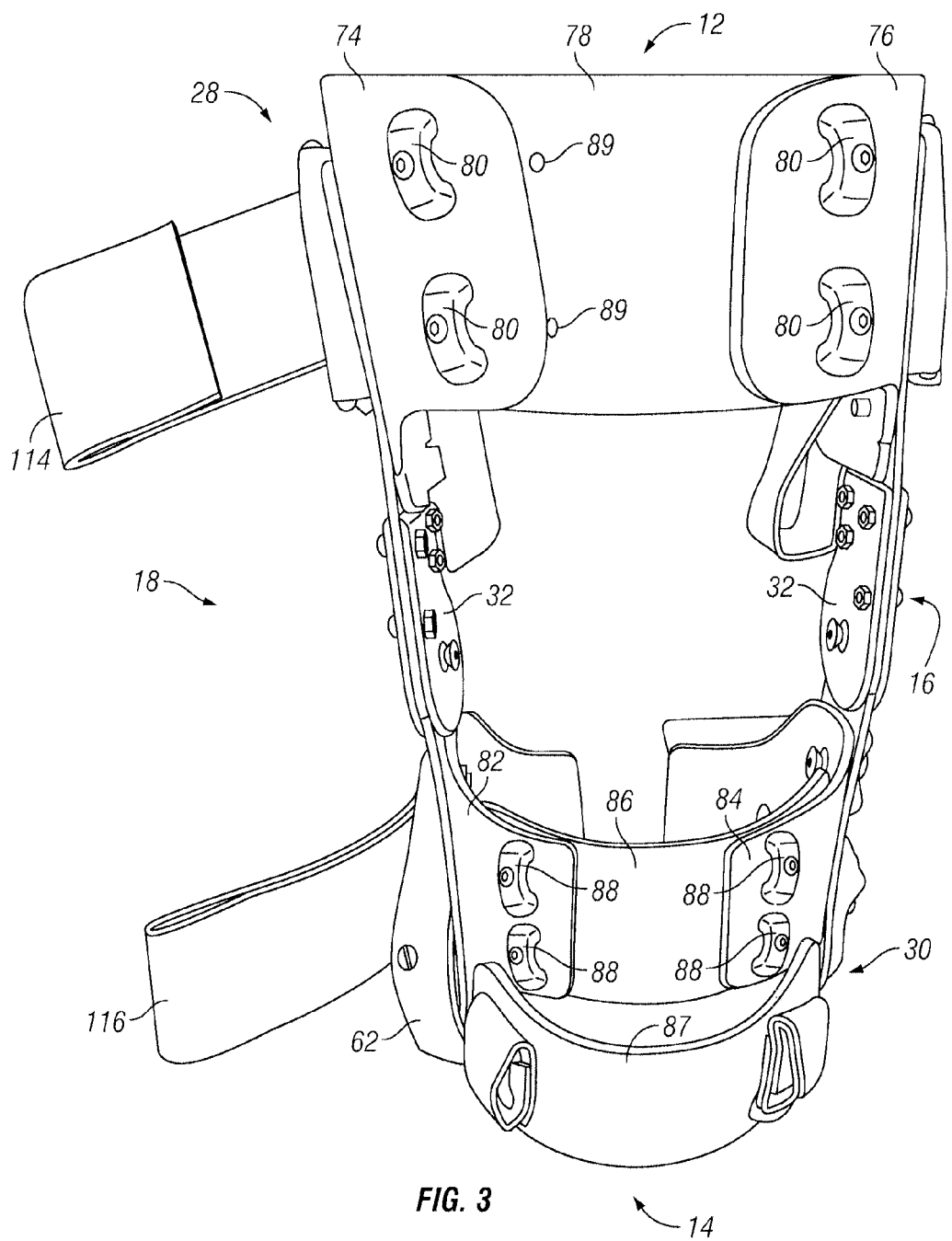
FIG. 3 is an anterior view of the example knee brace assembly shown in FIG. 1 with the straps and sleeve removed.
Figure 4:
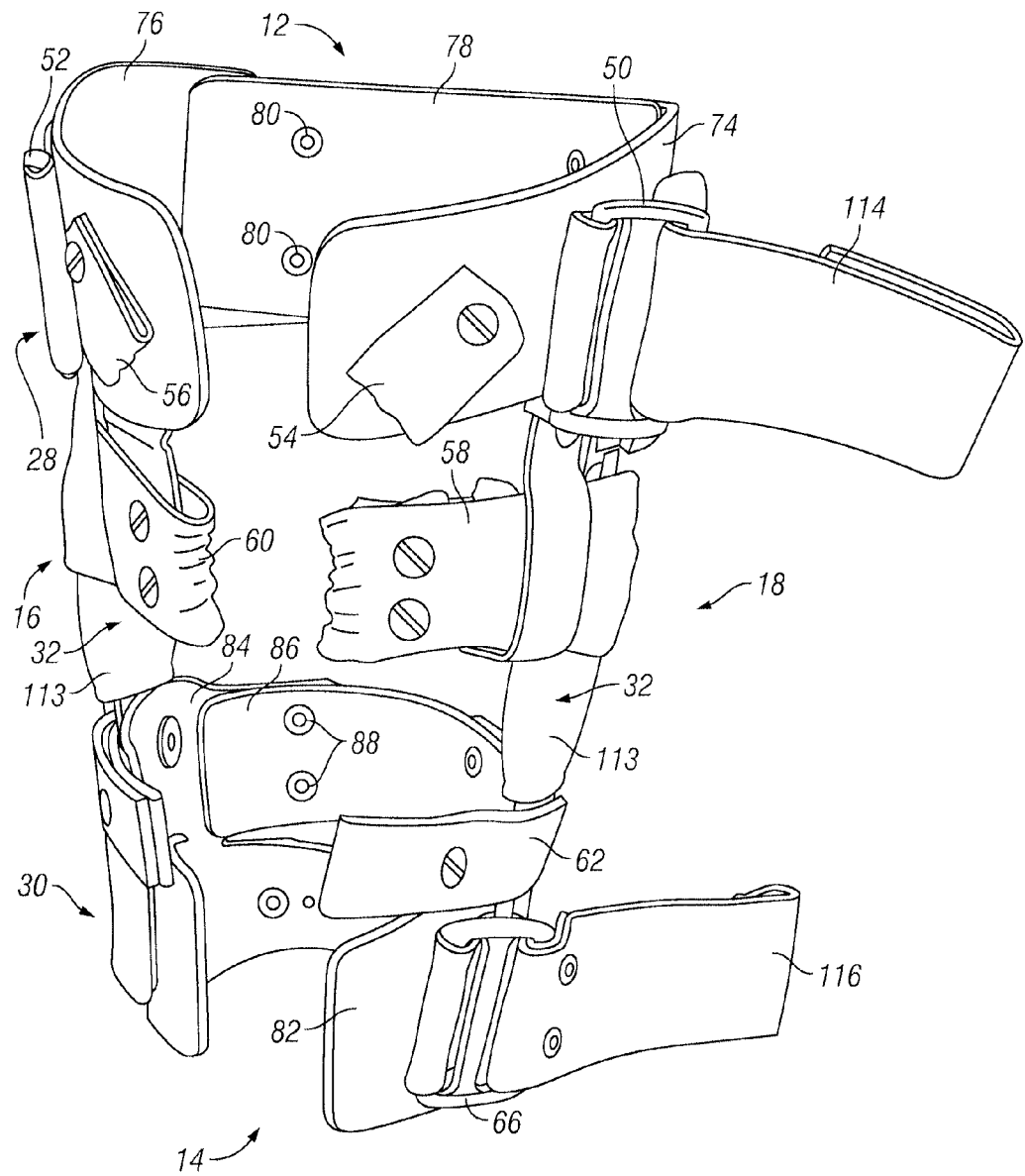
FIG. 4 is a posterior view of the example knee brace assembly shown in FIG. 3.
Figure 5:
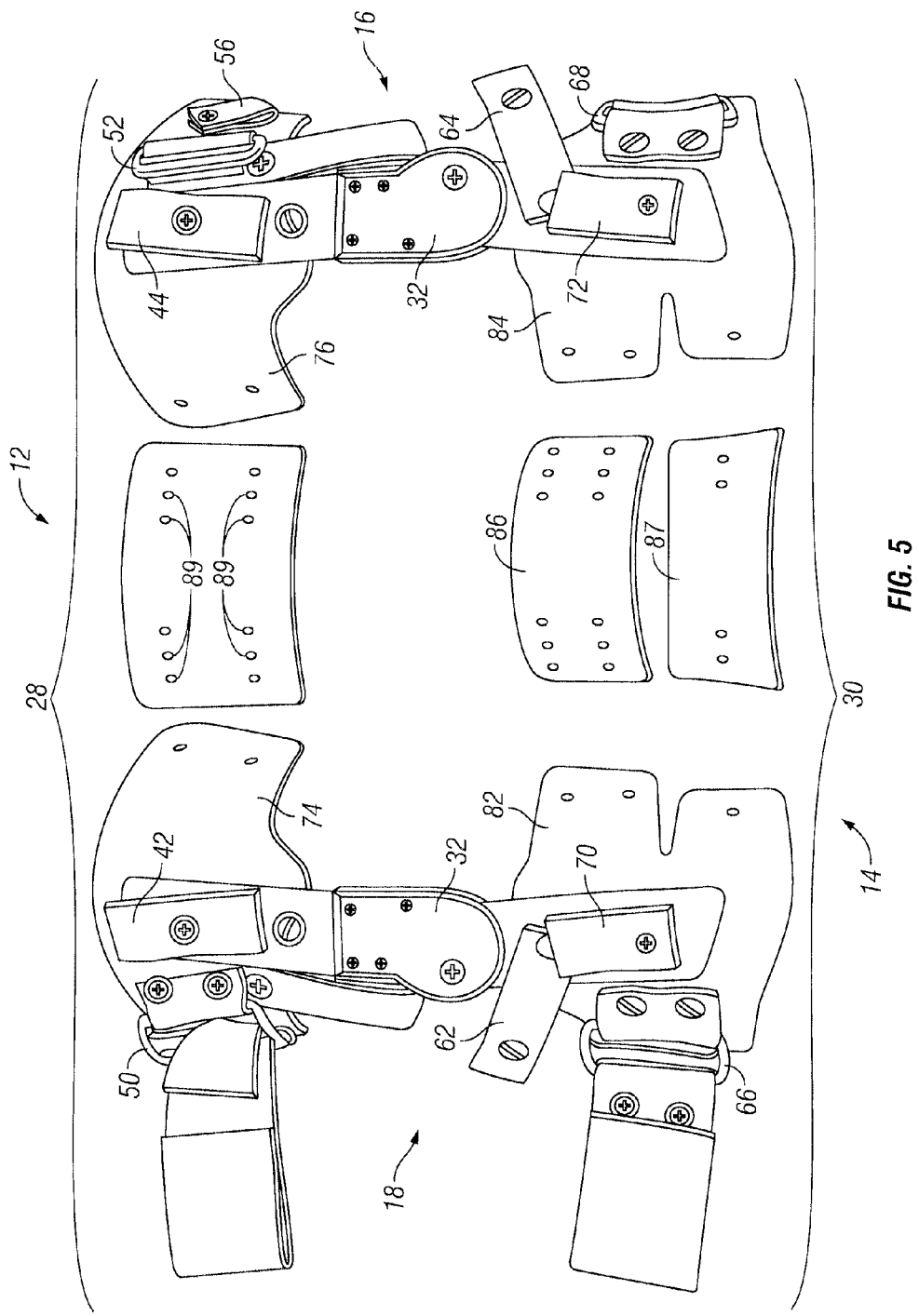
FIG. 5 is an anterior view of the example knee brace assembly shown in FIG. 3 in a partially disassembled state.

FIGS. 3 and 4 show the knee brace assembly 10 with the sleeve 24 and straps 38, 40 removed. FIG. 5 shows the compression systems 28, 30 partially disassembled with the hinge assemblies 32. As shown, a proximal closure strap 114 and distal closure strap 116 can be seen. In the embodiment shown, the straps 114, 116 are attached to attachment anchors 50, 66 and can connect to closure loops 52, 68.

In this example, the proximal compression system 28 includes a proximal lateral compression plate 74 and a proximal medial compression plate 76 that are connected by a proximal medial to lateral connector 78 using fasteners 80. In this example, the distal compression system 30 includes a distal lateral compression plate 82 and a distal medial compression plate 84 that are connected by a first distal medial to lateral connector 86 and a second distal medial to lateral connector 87 using fasteners 88. In this example, the proximal/distal medial to lateral connectors 78, 86 include openings 89 so that the size of the compression systems 28, 30 can be adjusted to accommodate users with various sizes of users' thighs and calves.

The compression plates 74, 76, 82, 84 are positioned over major muscle groups at the thigh and calf to use the tight muscles as a stabile substrate for available natural strength. In one embodiment, as discussed below, the plates 74, 76, 82, 84 are plastic and come in a variety (e.g., 3) different densities of flex/stiffness and are interchangeable to create different levels of stability. The plates 74, 76, 82, 84 are designed to have a broad tissue coverage grid for better compression strength and provide a stabile surface to prevent the straps 38, 40 and frame from sinking into tissue and losing strength and providing a surface for anchoring straps. The compression plates 74, 76, 82, 84 along with the struts of the hinge assemblies 32 are designed to provide medial and lateral stability when the system is tight.

The connectors' 78, 86 purpose is to connect the proximal and distal medial and lateral compression plates 74, 76, 82, 84 and keep them in position. The first distal medial to lateral connector 86 is designed as the primary stabilizing component to hold the proximal tibia in place. The compression plates 74, 76, 82, 84 may come in various different levels of flex/stiffness to regulate different levels of flexibility to establish different levels of stability.

The proximal compression system 28 and the distal compression system 30 are pivotally connected with hinge assemblies 32. As discussed below with regard to FIGS. 8-14, the hinge assemblies 32 are configured to allow rotation of the proximal compression system 28 with respect to the distal compression system 30 when the user's leg is in flexion to allow rotation of the thigh with respect to the calf, but limit or prevent rotation when the leg is extended. This allows a more natural movement for the user than a rigid hinge would allow.

The configuration of proximal/distal compression systems 28, 38 with the first and second straps 38, 40 provide leverage to apply compression to the soft tissue in the thigh and calf and provide limiting stability to the ACL and PCL to augment stability at the proximal tibia. When the leg is extending, the first strap 38 and second strap 40 pull the proximal and distal compression plates tight against the leg. This action compresses soft tissue "muscle groups" at the thigh and calf and stiffens the frame to create upper level stability. When the leg flexes, the compression systems 28, 30 expand allowing comfort and mobility in flexion. Thus, the assemblies 28, 30 compress in extension and expand in flexion in conjunction with the straps 38, 40.

The first strap 38 and the second strap 40 may also provide a limiting function. As the second strap 40 pulls tight in extension applying leverage around the proximal compression plates 74, 76 and the distal compression plates 82, 84 and goes around first distal medial to lateral connector 86 compressing it and pulling posterior to augmenting stability for the ACL. The first strap 38 pulls to apply leverage around the proximal compression plates 74, 76 and distal compression plates 82, 84 and pulls longitudinally or parallel to the longitudinal axis of the legs posterior in extension providing strength to the PCL to prevent hyperextension. In one embodiment, this limits from approximately 25 degrees in extension and expands in flexion. As discussed above, the level of stability can be adjusted by changing the tightness of the first and second straps 38, 40 at the connectors. Each strap 38, 40 can be adjusted individually to pinpoint stability to the area of stability need without over tightening the entire support to maintain comfort and mobility.

Figure 6:
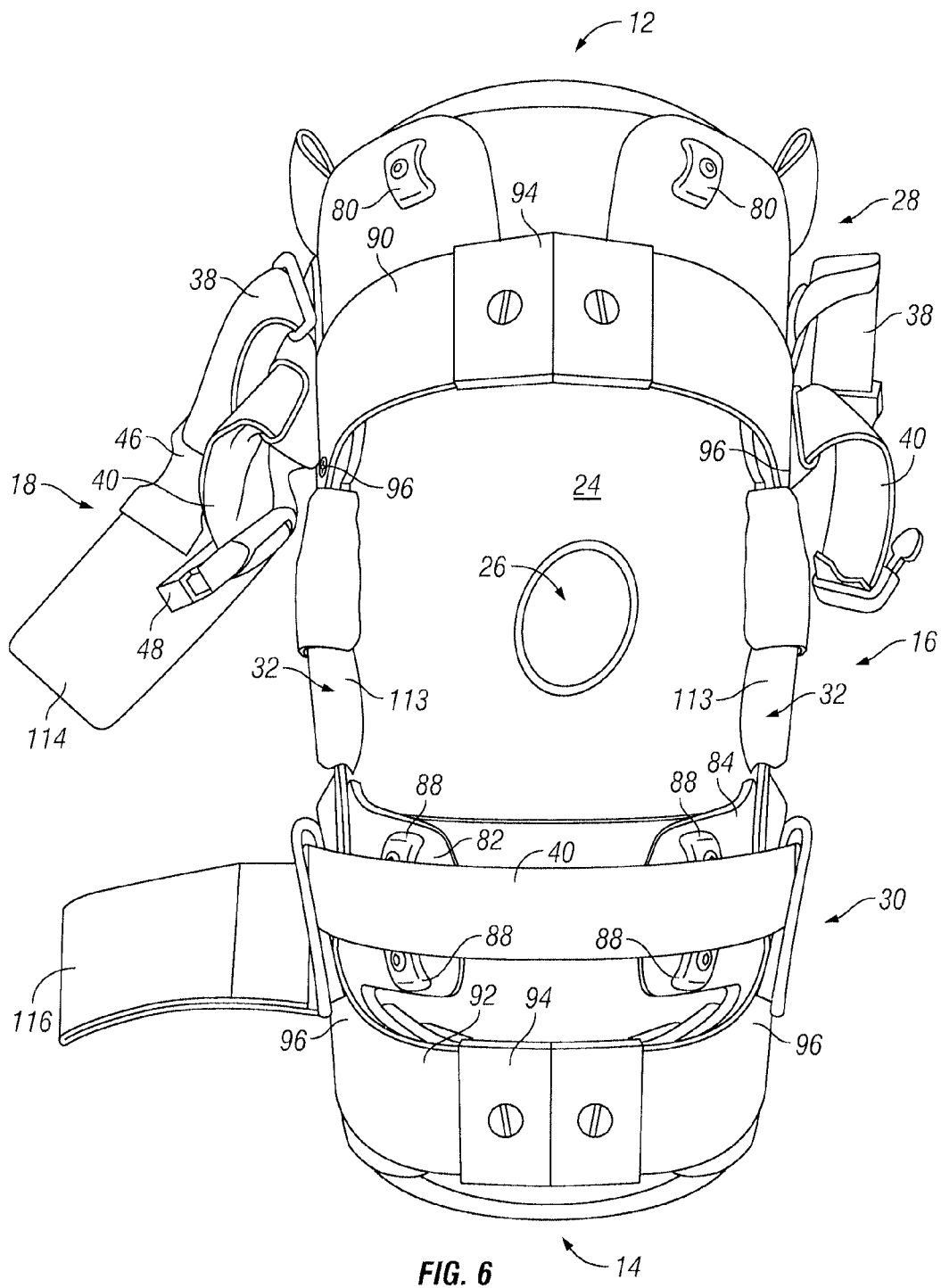
FIG. 6 is an anterior view of an example knee brace assembly with optional add-on medial-lateral connectors according to an embodiment of the invention.
Figure 7:
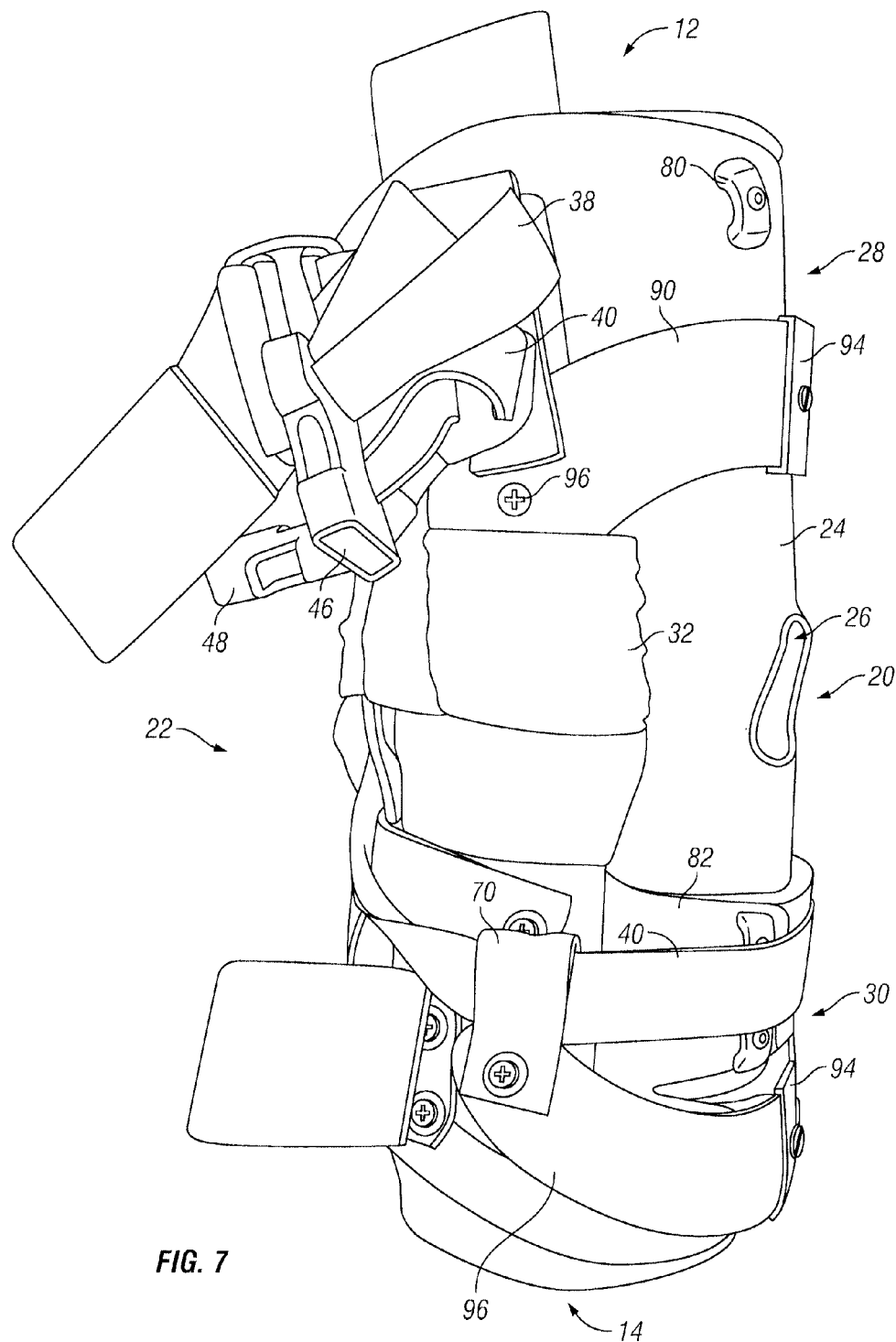
FIG. 7 is a lateral view of the example knee brace assembly shown in FIG. 6.
Figure 8:
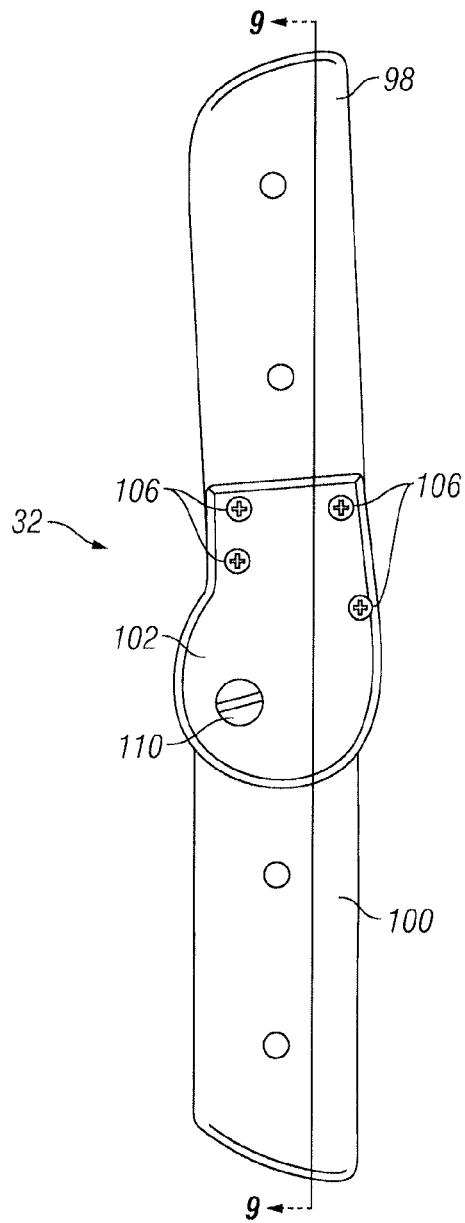
FIG. 8 is a side view of an example hinge assembly that could be used with the knee brace assembly according to an embodiment of the invention.
Figure 9:
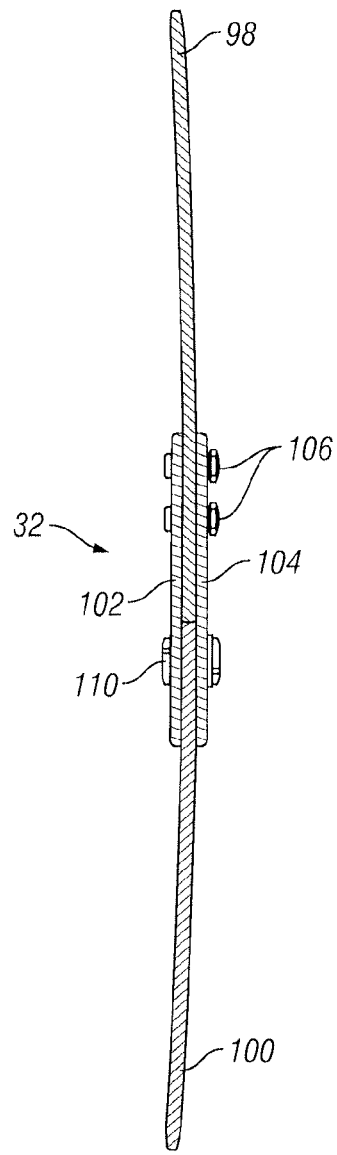
FIG. 9 is a cross-section view of the example hinge assembly shown in FIG. 8 along line 9-9.
Figure 10:
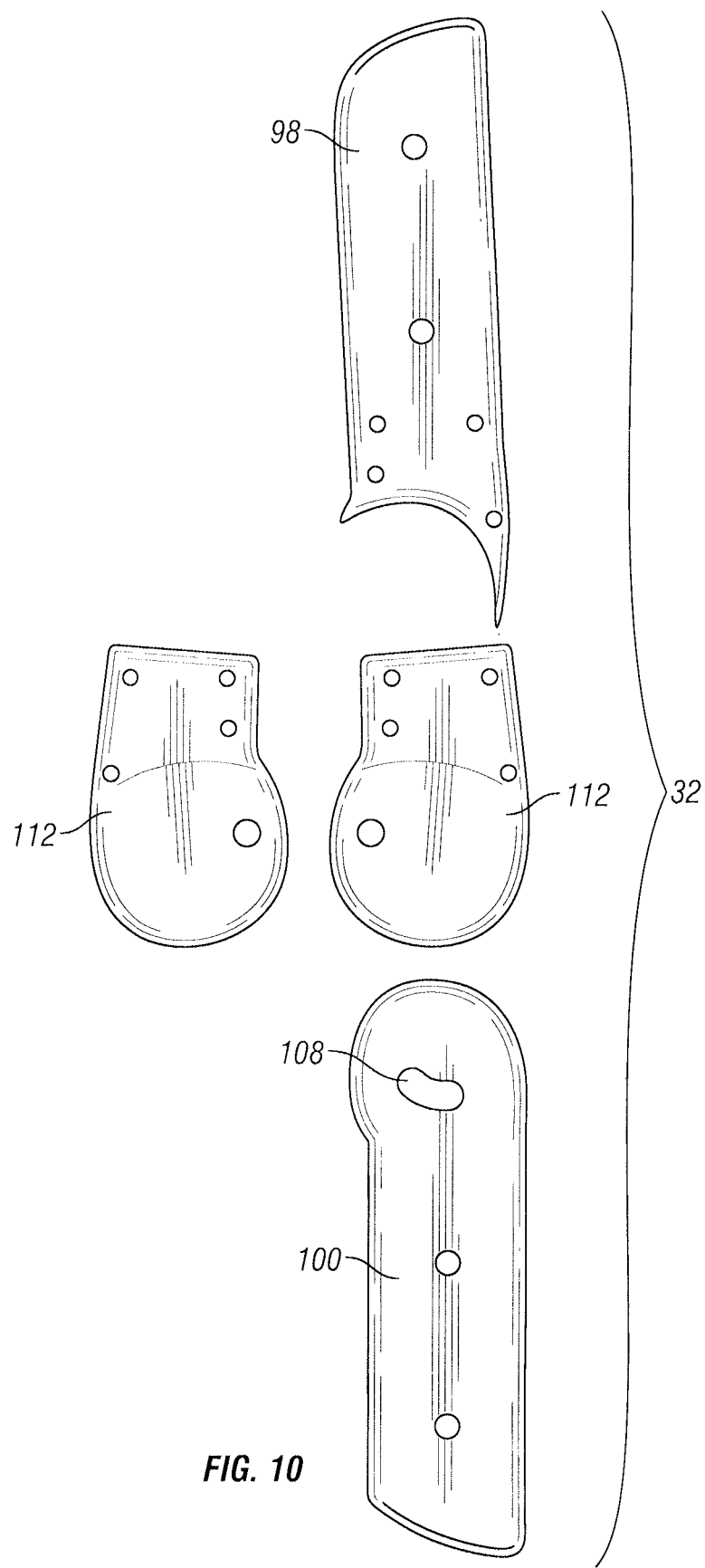
FIG. 10 is a side view of the example hinge assembly shown in FIG. 8 in a disassembled state.

In one embodiment, the compression systems 28, 30 provide modular stability that may be customized for a particular user's needs. For example, the distal and/or proximal compression plates 74, 76 82, 84 and/or distal and/or proximal connectors 78, 86 may be formed from plastic with various levels of plate density of flexibility that can be changed to allow create various different levels of stability. This allows a physician to mix and match stability range from post op, through the rehab process and change stability needs for long term use during the user's specified sports activity. Additionally, as seen in the example shown in FIG. 6, there may be an add-on proximal metal cross member 90 and/or a distal metal cross member 92 that can be added to create an additional level or maximum stability for medial and lateral protection. The add-on cross members 90, 92 may have proximal and distal articulating middle connectors 94 that move up and down and could be adjusted for different leg diameters. The cross members 90, 92 may be connected non-statically at distal struts 96 to allow the cross members 90, 92 with a screw to articulate with the frame that allow the frame to flex and prevent from constraining the joint. Modular components allow a variety of options to match specific instabilities of the user with the user's specific level of sports demand.

FIGS. 8-14 show various components of an example hinge assembly 32 that could be used with the knee brace assembly 10 to increase natural movement of the user by allowing rotation when the user's leg is in flexion while preventing rotation in extension. In this example, the hinge assembly 32 includes a proximal strut 98 and a distal strut 100. As shown, the proximal strut 98 is connected with an inside hinge plate 102 and an outside hinge plate 104 using fasteners 106. The distal strut 100 includes an arcuate slot 108 that is dimensioned to receive a pin 110 to provide limited angular movement between the distal strut 100 and the proximal strut 98. In this example, the proximal strut 98 and distal strut 100 are a free floating joint connected together by a pin 110. Typically, the hinge assembly 32 is made of metal construction for medial and lateral stability. In some cases, the hinge assembly 32 may be covered with a hinge sleeve 113, such as a neoprene sleeve.

In this example, the hinge plates 102, 104 include undulating cam surfaces 112 that allow the distal strut 100 to move freely (including rotation about a longitudinal axis) inside the plates 102, 104 corresponding to when the user's leg is in flexion to allow relative rotation between the proximal compression system 28 and the distal compression system 30 in flexion. As the hinge assembly 32 returns to extension, the cam surfaces 112 on the hinge plates 102, 104 are configured to gradually reduce rotation between the distal strut 100 and the proximal strut 98. In one embodiment, from around 25 degrees to full extension of the user's leg, the cam surfaces 112 on the plates 102, 104 are configured to prevent any rotation to stabilize the joint. This is an improvement over rigid braces that restrict natural, kinematic movements of the thigh and calf. In the hinge assembly 32, the thigh and calf may move independently to allow the tibia to rotate on the femur in flexion and stabilizes in extension. This allows natural kinematics for mobility but provides stability and support at the proximal tibia.

Figure 15:
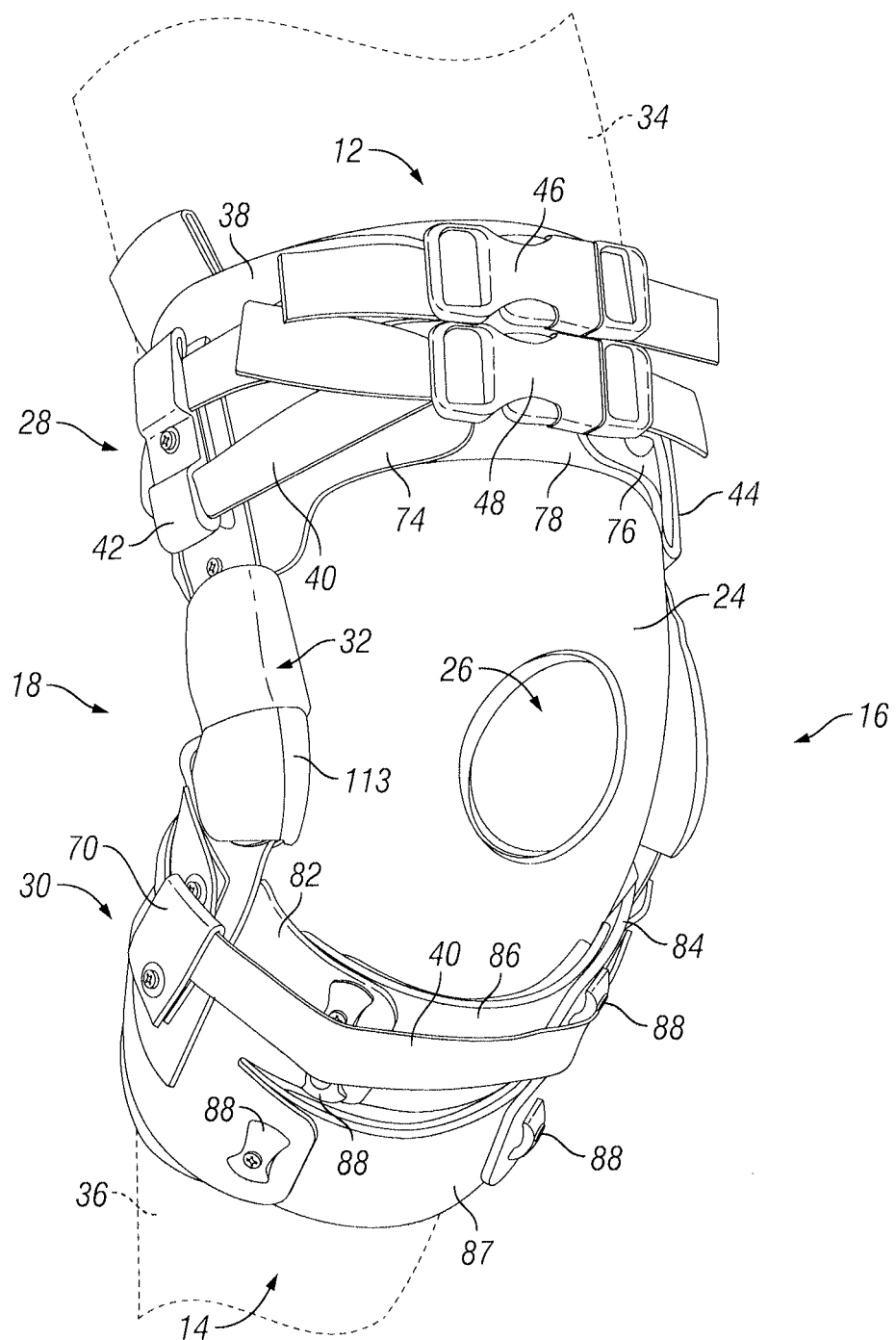
FIG. 15 is an anterior view of an example knee brace assembly according to an embodiment of the invention with a knee in flexion.
Figure 16:
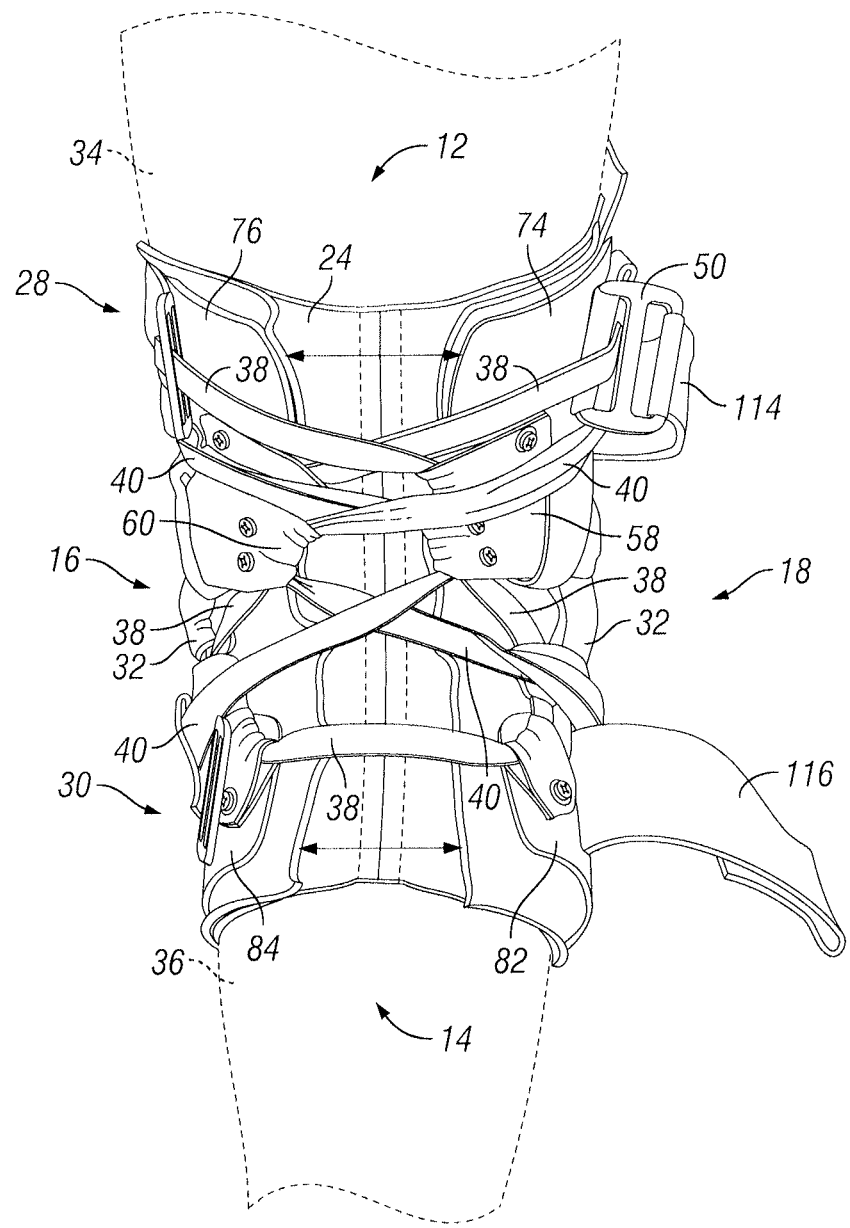
FIG. 16 is a posterior view of the example knee brace assembly shown in FIG. 15 with a knee in flexion.
Figure 17:
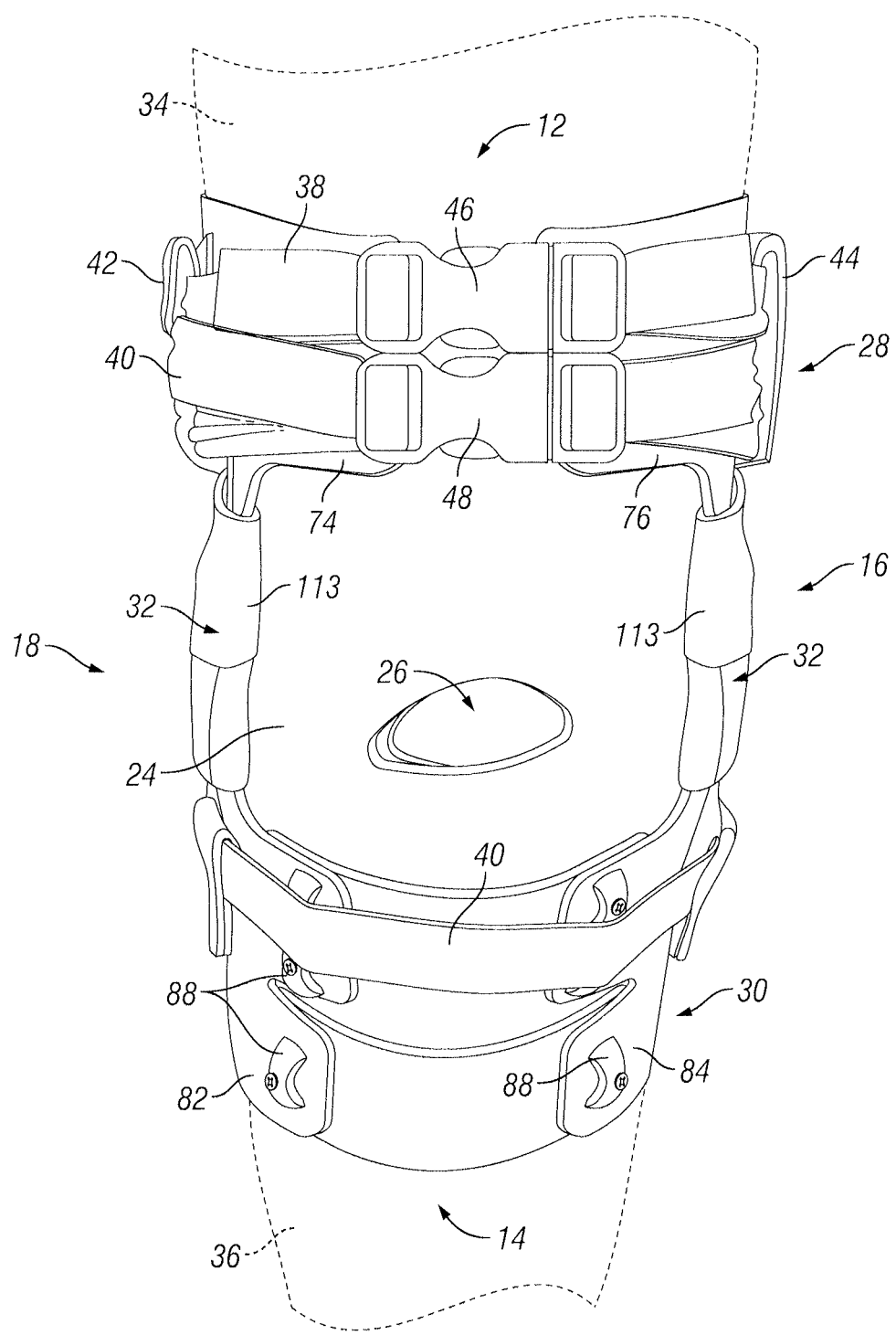
FIG. 17 is an anterior view of the example knee brace assembly shown in FIG. 15 with the knee in extension.
Figure 18:
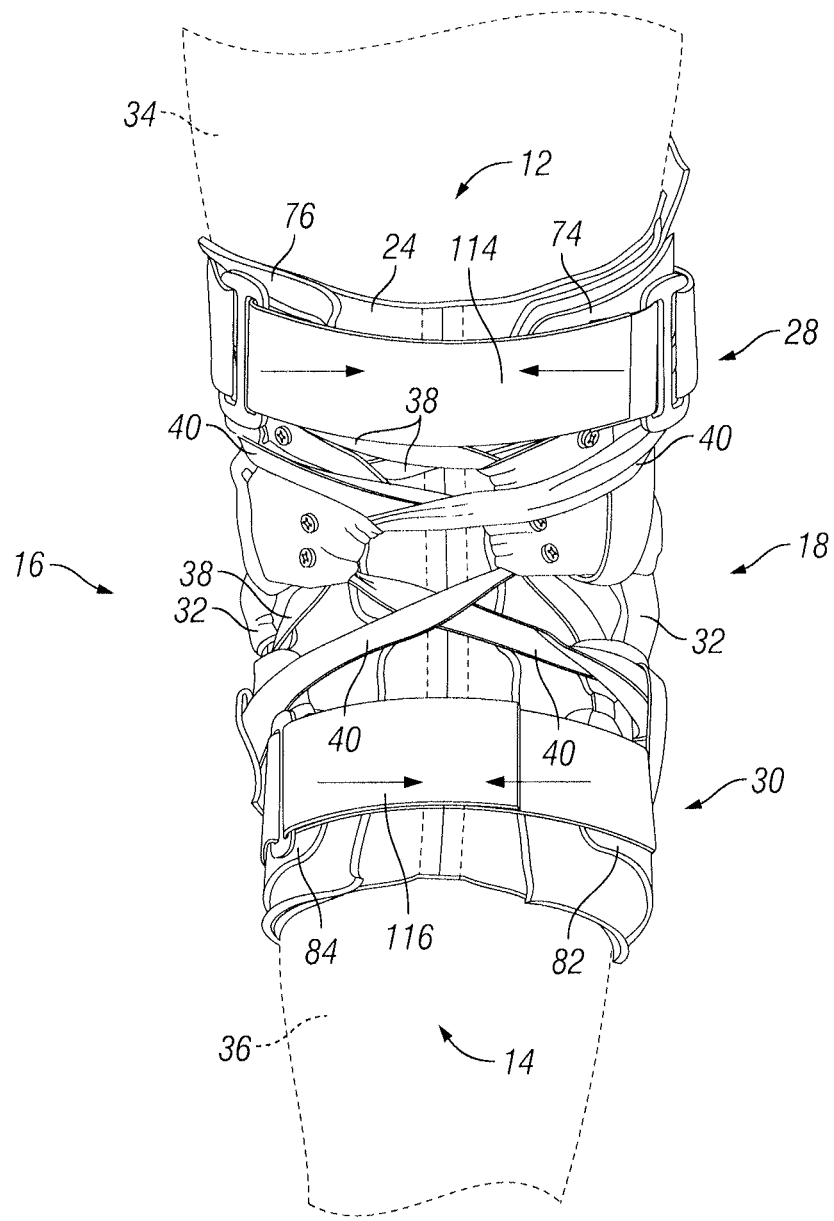
FIG. 18 is a posterior view of the example knee brace assembly shown in FIG. 15 with a knee in extension.
Figure 19:
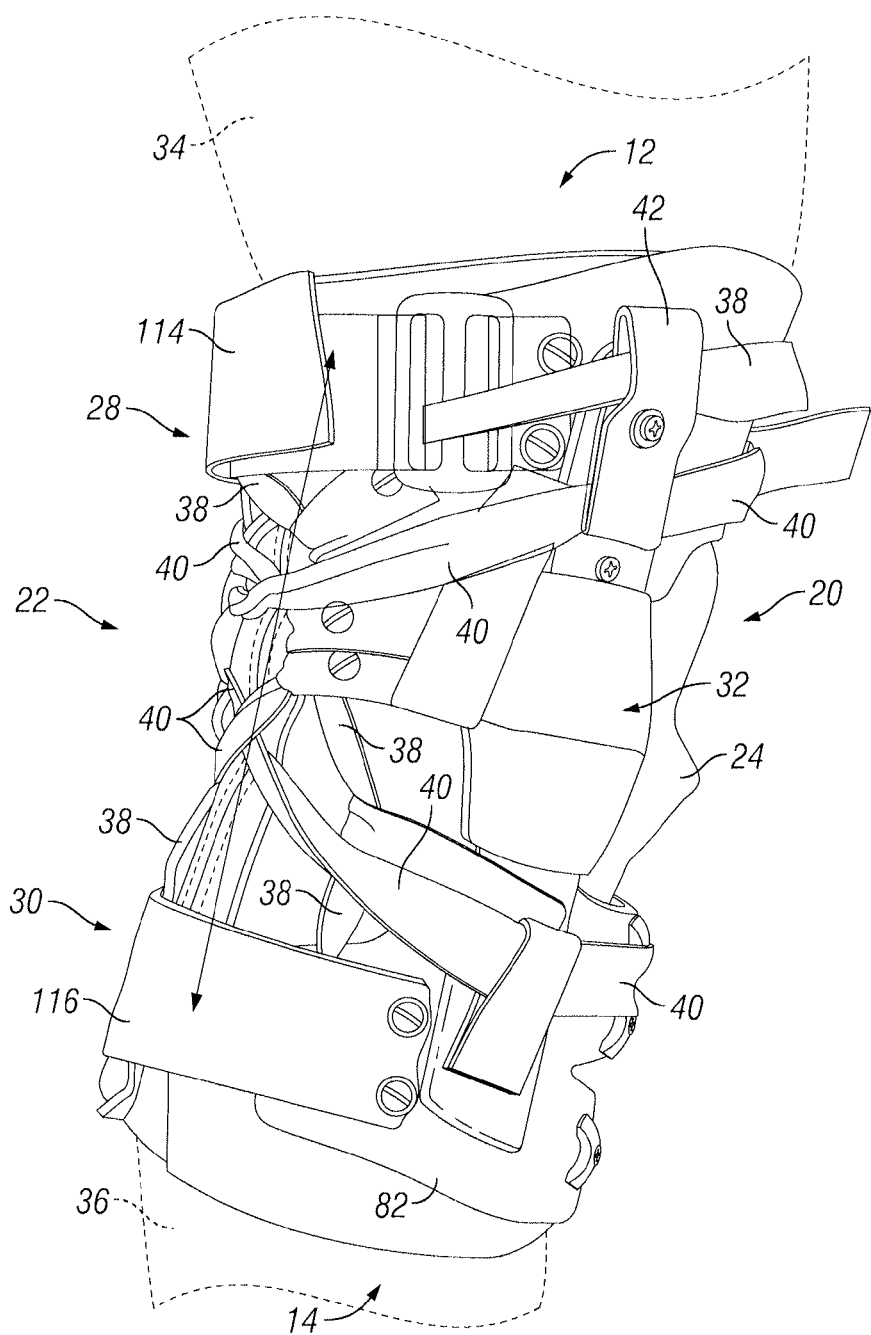
FIG. 19 is a lateral view of the example knee brace assembly shown in FIG. 15 with a knee in extension.

FIGS. 15-16 show the example knee brace assembly 10 with the user's knee in flexion and FIGS. 17-19 show the user's knee in extension. When the leg extends, the proximal and distal compression systems 28, 30 are activated by straps 38, 40—the compression plates 74, 76, 82, 84 tighten around the thigh and calf. The proximal and distal compression plates 74, 76, 82, 84 are still allowed flex to allow independent rotation at the thigh and calf that in turn allows the user to have superior pivoting movement. The non-mechanical tracking free floating hinge assembly 32 has cam surfaces 112 on the inside and outside plates 102, 104 that allow the hinge assembly 32 to have rotation in flexion to allow the tibia to rotate on the femur in flexion. As the leg returns to extension, the hinge assembly 32 gradually reduces rotation. In one embodiment, the hinge assembly 32 reduces rotation from approximately 25 degrees to full extension so the hinge assembly 32 is stabile does not allow rotation at the joint. The upper and lower compression plates 74, 76, 82, 84 transfer the stability to the joint space for continuous stability in flexion and extension.

The first and second straps 38, 40 are placed around and the compression plates 74, 76, 82, 84 in strap captures in leverage positions that pull the compression plates 74, 76, 82, 84 tight against the thigh and calf as the leg goes into extension to compress soft tissue. Both straps 38, 40 have buckles 46, 48 at the proximal anterior surface of the compression plates 74, 76, 82, 84 and can be tightened individually to focus on a specific instability or tightened to allow greater compression for a higher level of stability. The system is activated when the leg is going into extension by pulling the straps 38, 40 tight, as the leg returns to flexion the system relaxes allowing the compression plates 74, 76, 82, 84 to expand and allow mobility.

The second strap 40 provides stability to the ACL by using leverage around the proximal anterior and distal anterior frame and strut anchors 58, 60, 62, 64. When the leg is going into extension, it pulls the first distal medial to lateral connector 86 posterior to augment stability to the ACL.

The first strap 38 provides stability to the PCL by using the same type of leverage as the second strap 40. As the leg goes into extension the first strap 38 pulls tight posterior longitudinal or parallel to the leg to provide stability to the PCL. As the pressure increases from the anterior side, either by contact or force, stability increases to provide hyperextension support to the PCL.

Although the present disclosure has been described with reference to particular means, materials, and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A knee brace assembly comprising:
a proximal compression system adapted to be secured to a thigh;
a distal compression system adapted to be secured to a calf;
a proximal medial strap capture and a proximal lateral strap capture attached to the proximal compression system;
a medial leverage strut anchor and a lateral leverage strut anchor attached to the proximal compression system;
a distal medial strap capture and a distal lateral strap capture attached to the distal compression system;
a distal medial strut anchor and a distal lateral strut anchor attached to the distal compression system;
a lateral hinge assembly connecting a lateral portion of the proximal compression system and a lateral portion of the distal compression system to permit rotational movement of the proximal compression system with respect to the distal compression system;
a medial hinge assembly connecting a medial portion of the proximal compression system and a medial portion of the distal compression system to permit rotational movement of the proximal compression system with respect to the distal compression system; and
a first inelastic strap extending around the proximal compression system and the distal compression system, wherein the first strap crosses around the proximal compression system with a first segment extending from a medial position into the proximal lateral strap capture and a second segment extending from a lateral position into the proximal medial strap capture, wherein the first segment extends from the proximal lateral strap capture into the lateral leverage strut anchor, wherein the first segment extends from the lateral leverage strut anchor to the distal lateral strut anchor and extends around a medial side of the distal compression system, wherein the second segment extends from the proximal medial strap capture to the medial leverage strut anchor, wherein the second segment extends from the medial leverage strut anchor to the distal medial strut anchor and extends around a lateral side of the distal compression system;
a second inelastic strap extending around the distal compression system and the proximal compression system, wherein the second strap crosses around the distal compression system with a third segment extending into the distal medial strap capture and a fourth segment extending into the distal lateral strap capture, wherein the third segment extends from the distal medial strap capture to the lateral leverage strut anchor and extends around a medial side of the proximal compression system, wherein the fourth segment extends from the distal lateral strap capture to the medial leverage strut anchor and extends around a lateral side of the proximal compression system; and
wherein the first strap and the second strap are is leveraged by the distal medial strap capture, distal lateral strap capture, proximal medial strap capture, proximal lateral strap capture, medial leverage strut anchor, lateral leverage strut anchor, distal medial strut anchor, and distal lateral strut anchor to tighten the proximal compression system and the distal compression system to compress soft tissue in the thigh and calf when the leg is extended, but to release the proximal compression system and the distal compression system when the leg is in flexion.

2. The knee brace assembly of claim 1, wherein the lateral hinge assembly and the medial hinge assembly are configured to provide more than one axis of rotation when the leg is in flexion, but only provide one axis of rotation when the leg is extended.

3. The knee brace assembly of claim 1, wherein the lateral hinge assembly and the medial hinge assembly are configured to rotate about a longitudinal axis of each respective hinge assembly when the leg is in flexion.

4. The knee brace assembly of claim 1, wherein at least one of the lateral hinge assembly or the medial hinge assembly include a cam surface that restricts movement to a single axis when the leg is extended, but allows movement in more than one axis when the leg is in flexion.

5. The knee brace assembly of claim 1, wherein the lateral hinge assembly and the medial hinge assembly are configured to allow the thigh and calf may move independently to allow the tibia to rotate on the femur when the leg is in flexion, but stabilizes in extension.

6. The knee brace assembly of claim 1, wherein at least one of the lateral hinge assembly or the medial hinge assembly include a proximal strut and a distal strut, further comprising a pin pivotally connecting proximal strut with the distal strut, wherein the proximal strut and the distal strut are moveable with respect to each other about an axis other than a longitudinal axis of the pin when the leg is in flexion, but a cam surface restricts movement of the proximal strut and the distal strut to rotation only about the pin when the leg is extended.

7. The knee brace assembly of claim 6, further comprising a first plate and a second plate surrounding a connection between the proximal strut and the distal strut, wherein at least one of the first plate or the second plate include a cam surface that restricts movement of the distal strut with respect to the proximal strut.

8. The knee brace assembly of claim 7, wherein the cam surface restricts movement of the distal strut with respect to the proximal strut to pivotally about the longitudinal axis of the pin when the leg is in extension, but allows free movement between the distal strut and the proximal strut when the leg is in flexion.

9. The knee brace assembly of claim 1, wherein at least one of the proximal compression system or the distal compression system includes a medial compression plate and a lateral compression plate joined by a medial to lateral connector.

10. The knee brace assembly of claim 9, wherein the medial compression plate and the lateral compression plate are formed from plastic.

11. The knee brace assembly of claim 10, further comprising a metal add-on connector that is connected to the medial compression plate and the lateral compression plate.

12. The knee brace assembly of claim 9, wherein the medial compression plate and the lateral compression plate are configured to compress soft tissue surrounding the knee when the leg is in extension.

13. The knee brace assembly of claim 12, further comprising a plurality of compression plates having varying flexibilities that can be selectively chosen to vary stability of the knee brace assembly.

14. A knee brace assembly comprising:
a proximal compression system adapted to be secured to a thigh;
a distal compression system adapted to be secured to a calf;
a proximal medial strap capture and a proximal lateral strap capture attached to the proximal compression system;
a medial leverage strut anchor and a lateral leverage strut anchor attached to the proximal compression system;
a distal medial strap capture and a distal lateral strap capture attached to the distal compression system;
a distal medial strut anchor and a distal lateral strut anchor attached to the distal compression system;
a lateral hinge assembly connecting a lateral portion of the proximal compression system and a lateral portion of the distal compression system to permit rotational movement of the proximal compression system with respect to the distal compression system, wherein the lateral hinge assembly is configured to provide more than one axis of movement when the leg is in flexion, but only provide one axis of rotation when the leg is extended;
a medial hinge assembly connecting a medial portion of the proximal compression system and a medial portion of the distal compression system to permit rotational movement of the proximal compression system with respect to the distal compression system, wherein the lateral hinge assembly is configured to provide more than one axis of movement when the leg is in flexion, but only provide one axis of rotation when the leg is extended;
a first inelastic strap extending around the proximal compression system and the distal compression system, wherein the first strap crosses around the proximal compression system with a first segment extending from a medial position into the proximal lateral strap capture and a second segment extending from a lateral position into the proximal medial strap capture, wherein the first segment extends from the proximal lateral strap capture into the lateral leverage strut anchor, wherein the first segment extends from the lateral leverage strut anchor to the distal lateral strut anchor and extends around a medial side of the distal compression system, wherein the second segment extends from the proximal medial strap capture to the medial leverage strut anchor, wherein the second segment extends from the medial leverage strut anchor to the distal medial strut anchor and extends around a lateral side of the distal compression system;
a second inelastic strap extending around the distal compression system and the proximal compression system, wherein the second strap crosses around the distal compression system with a third segment extending into the distal medial strap capture and a fourth segment extending into the distal lateral strap capture, wherein the third segment extends from the distal medial strap capture to the lateral leverage strut anchor and extends around a medial side of the proximal compression system, wherein the fourth segment extends from the distal lateral strap capture to the medial leverage strut anchor and extends around a lateral side of the proximal compression system; and
wherein the first strap and the second strap are leveraged by the distal medial strap capture, distal lateral strap capture, proximal medial strap capture, proximal lateral strap capture, medial leverage strut anchor, lateral leverage strut anchor, distal medial strut anchor, and distal lateral strut anchor to provide stability to the PCL and ACL by tightening the proximal compression system and the distal compression system to compress soft tissue in the thigh and calf when the leg is extended, but to release the proximal compression system and the distal compression system when the leg is in flexion.

15. The knee brace assembly of claim 14, further comprising a first buckle connecting the open ends of the first strap together, wherein the first buckle is configured to tighten and loosen the first strap.

16. The knee brace assembly of claim 15, further comprising a second buckle connecting the open ends of the second strap together, wherein the second buckle is configured to tighten and loosen the second strap.

17. The knee brace assembly of claim 16, wherein at least one of the lateral hinge assembly or the medial hinge assembly include a proximal strut and a distal strut, further comprising a pin pivotally connecting proximal strut with the distal strut, wherein the proximal strut and the distal strut are moveable with respect to each other about an axis other than a longitudinal axis of the pin when the leg is in flexion, but a cam surface restricts movement of the proximal strut and the distal strut to rotation only about the pin when the leg is extended.

18. The knee brace assembly of claim 17, further comprising one or more posterior anchors configured to receive at least one of the first strap or the second strap.

19. The knee brace assembly of claim 18, wherein at least one of the first strap or the second strap crosses upon itself.

20. A knee brace assembly comprising:
a proximal compression system adapted to be secured to a thigh;
a distal compression system adapted to be secured to a calf;
a proximal medial strap capture and a proximal lateral strap capture attached to the proximal compression system;
a medial leverage strut anchor and a lateral leverage strut anchor attached to the proximal compression system;
a distal medial strap capture and a distal lateral strap capture attached to the distal compression system;
a distal medial strut anchor and a distal lateral strut anchor attached to the distal compression system;

hinge means for pivotally connecting the proximal compression system and the distal compression system, wherein the hinge means is configured to allow the thigh and calf may move independently to allow the tibia to rotate on the femur when the leg is in flexion, but restricts movement of the proximal compression system with respect to the distal compression system to rotation about an axis when the leg is in extension;

a first inelastic strap extending around the proximal compression system and the distal compression system, wherein the first strap crosses around the proximal compression system with a first segment extending from a medial position into the proximal lateral strap capture and a second segment extending from a lateral position into the proximal medial strap capture, wherein the first segment extends from the proximal lateral strap capture into the lateral leverage strut anchor, wherein the first segment extends from the lateral leverage strut anchor to the distal lateral strut anchor and extends around a medial side of the distal compression system, wherein the second segment extends from the proximal medial strap capture to the medial leverage strut anchor, wherein the second segment extends from the medial leverage strut anchor to the distal medial strut anchor and extends around a lateral side of the distal compression system;

a second inelastic strap extending around the distal compression system and the proximal compression system, wherein the second strap crosses around the distal compression system with a third segment extending into the distal medial strap capture and a fourth segment extending into the distal lateral strap capture, wherein the third segment extends from the distal medial strap capture to the lateral leverage strut anchor and extends around a medial side of the proximal compression system, wherein the fourth segment extends from the distal lateral strap capture to the medial leverage strut anchor and extends around a lateral side of the proximal compression system; and wherein the first strap and the second strap are leveraged to tighten the proximal compression system and the distal compression system to compress soft tissue in the thigh and calf when the leg is extended, but to release the proximal compression system and the distal compression system when the leg is in flexion.

21. A knee brace assembly comprising:

a proximal compression system adapted to be secured to a thigh;

a distal compression system adapted to be secured to a calf;

one or more proximal connectors attached to the proximal compression system;

one or more distal connectors attached to the distal compression system;

a first inelastic strap routed between the proximal compression system and the distal compression system through at least a portion of the proximal connectors and the distal connectors, wherein the first inelastic strap has a first segment that extends from a medial position to a lateral position and a second segment that extends from a lateral position to a medial position to cross over each other on an anterior side of the knee brace assembly; and a second inelastic strap routed between the proximal compression system and the distal compression system through the proximal connectors and the distal connectors; wherein the second inelastic strap has a third segment that extends from a medial position to a lateral position and a fourth segment that extends from a lateral position to a medial position to cross over each other on an anterior side of the knee brace assembly; and wherein the proximal connectors and the distal connectors are arranged on the proximal compression system and distal compression system, respectively, to restrict movement of the first strap and the second strap in a manner that tightens the proximal compression system and the distal compression system to compress soft tissue in the thigh and calf when the leg is extended, but releases the proximal compression system and the distal compression system when the leg is in flexion.

* * * * *